United States Patent [19]

Matthews et al.

[11] Patent Number: 4,659,331

[45] Date of Patent: Apr. 21, 1987

[54] PROSTHESIS INTERFACE SURFACE AND METHOD OF IMPLANTING

[75] Inventors: Larry S. Matthews; Steven A. Goldstein, both of Ann Arbor, Mich.

[73] Assignee: Regents of University of Michigan, Ann Arbor, Mich.

[21] Appl. No.: 555,812

[22] Filed: Nov. 28, 1983

[51] Int. Cl.$^4$ .............................................. A61F 2/38
[52] U.S. Cl. .................................. 623/20; 623/22
[58] Field of Search ........... 128/92 C, 92 CA, 92 EB; 3/1.9, 1.911, 1.91, 1.912, 1.913; 623/16, 17, 18, 19, 20, 21, 22, 23

[56] References Cited

U.S. PATENT DOCUMENTS

| | | | |
|---|---|---|---|
| 2,910,978 | 11/1959 | Urist | 128/92 |
| 3,683,421 | 8/1972 | Martinie | 623/18 |
| 3,728,742 | 4/1973 | Averill et al. | 623/18 |
| 3,808,606 | 5/1974 | Tronzo | 3/1.9 |
| 3,840,904 | 10/1974 | Tronzo | 3/1.912 |
| 3,869,731 | 3/1975 | Waugh et al. | 623/20 |
| 4,021,864 | 5/1977 | Waugh | 623/20 |
| 4,166,292 | 9/1979 | Bokros | 623/18 |
| 4,231,120 | 11/1980 | Day | 623/18 |
| 4,309,777 | 1/1982 | Patil | 623/17 |
| 4,355,429 | 10/1982 | Mittelmeier et al. | 128/92 C |
| 4,532,660 | 8/1985 | Fields | 623/18 |

FOREIGN PATENT DOCUMENTS 1383474  2/1975  United Kingdom ................. 3/1.911

OTHER PUBLICATIONS

"Compartmental II Total Knee" brochure Zimmer, 1976, B 260 20M276.

Primary Examiner—Richard J. Apley
Assistant Examiner—David J. Isabella
Attorney, Agent, or Firm—Rohm & Monsanto

[57] ABSTRACT

An improved prosthesis interface surface is incorporated on any implantable component where stable long lasting bone fixation is needed. The surface achieves immediate stabilization of the prosthetic component and promotes bony tissue ingrowth by either making the surface of a porous metal or ceramic or coating the surface of the interface surface with a porous metal or ceramic. In the preferred embodiment, the surface includes a large number of conical protrusions which are specifically designed to resist shear and torsional disruptive forces while accommodating the compression loads that occur during motion of a joint prosthesis. By utilizing a series of conical protrusions, the surface contact area of the interface surface is much greater than interface surfaces now in use and this large surface contact area improves stability and provides a large area for secure bony ingrowth fixation. The improved prosthesis interface surface of the present invention may be used in hip, knee, ankle and shoulder joint replacement components as well as in any other implant component which is to be secured in trabecular bone. Additionally, the interface surface may be used to implant artificial dentures and for bony insertions of artificial ligaments and tendons. In another aspect of the present invention, a method of implanting artificial joints utilizing the improved prosthesis interface surface includes, in one embodiment, the use of a drill guide, and in another embodiment, a pilot driver.

12 Claims, 16 Drawing Figures

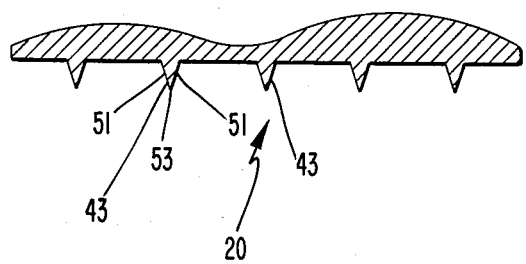
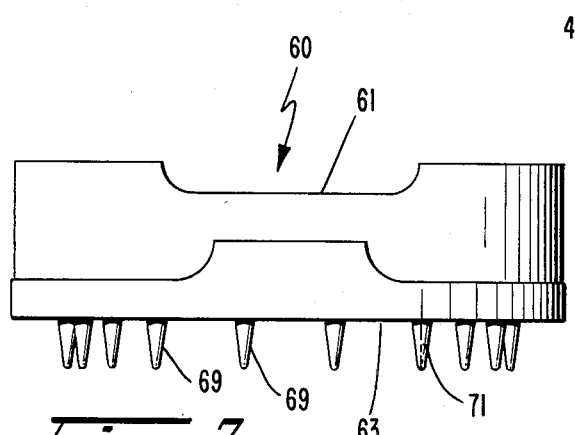
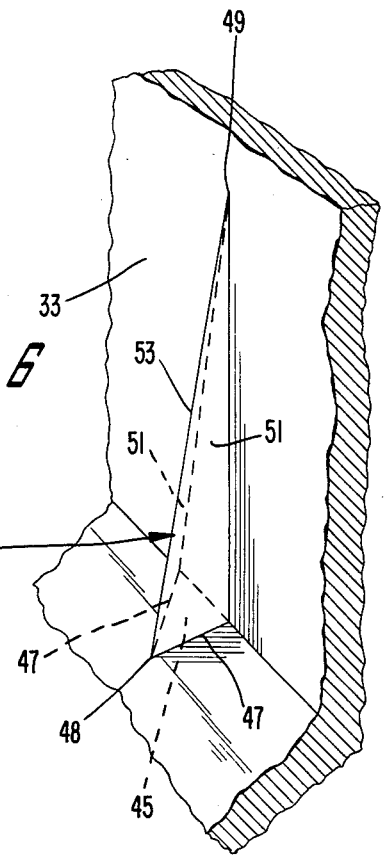
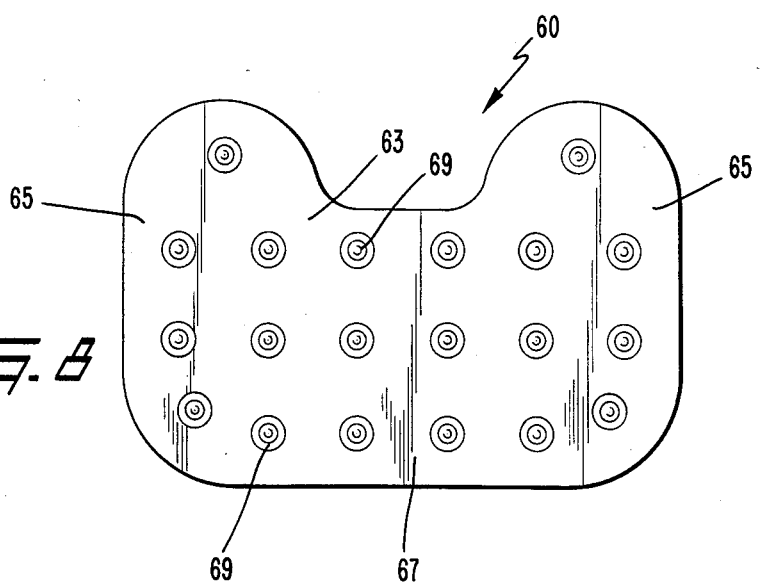

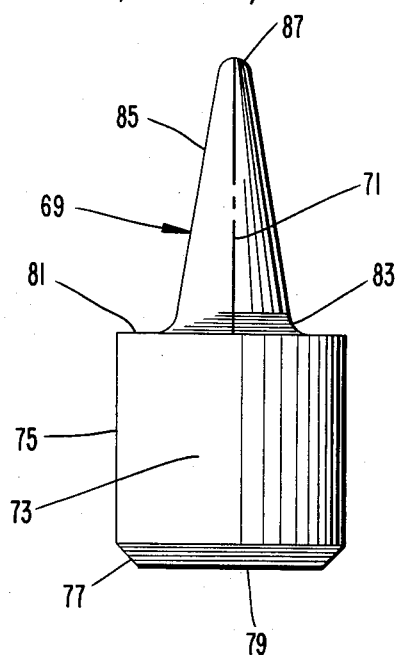
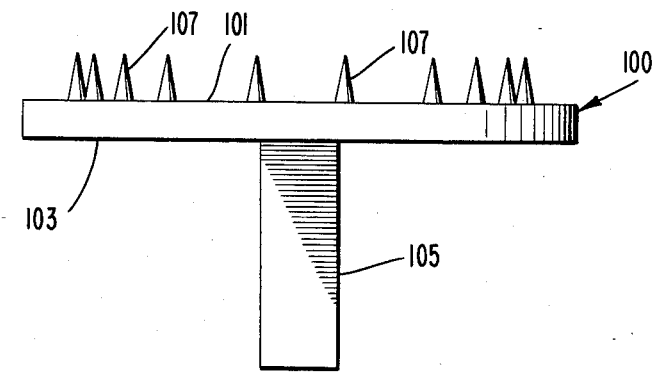
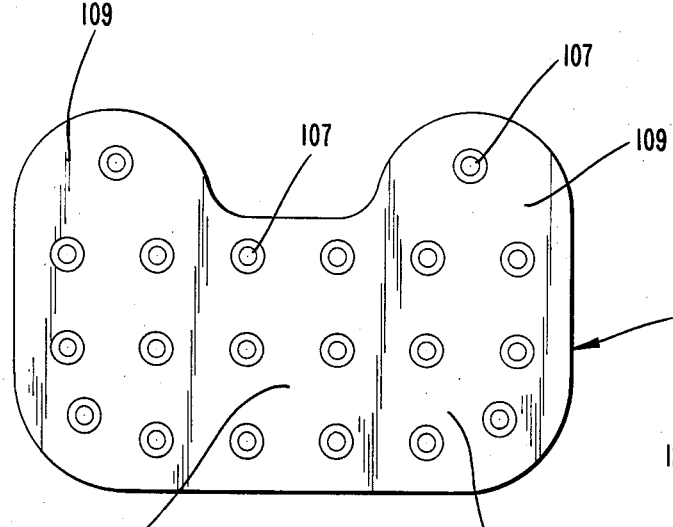
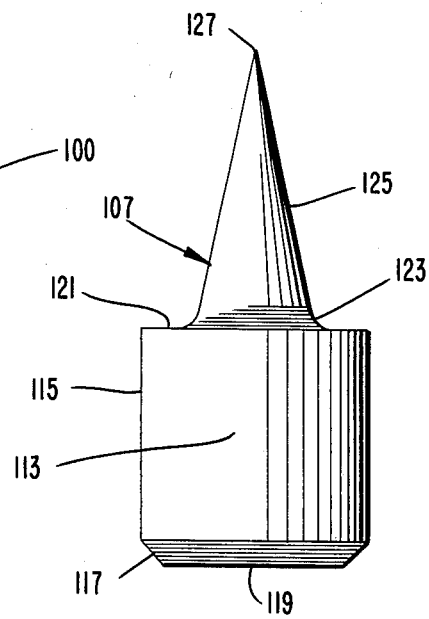

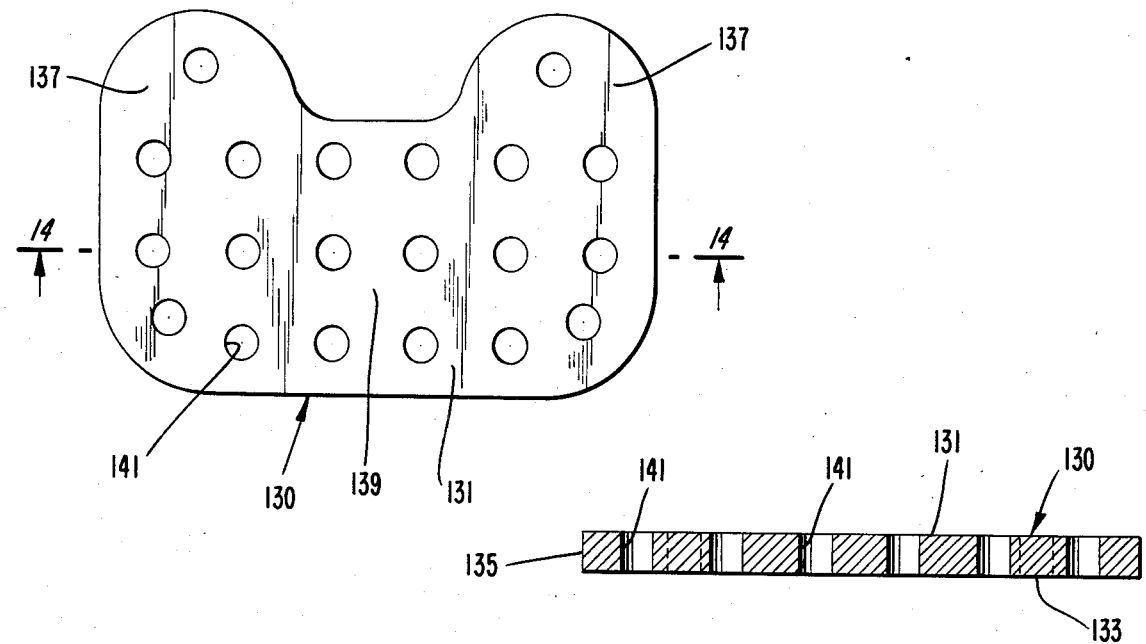
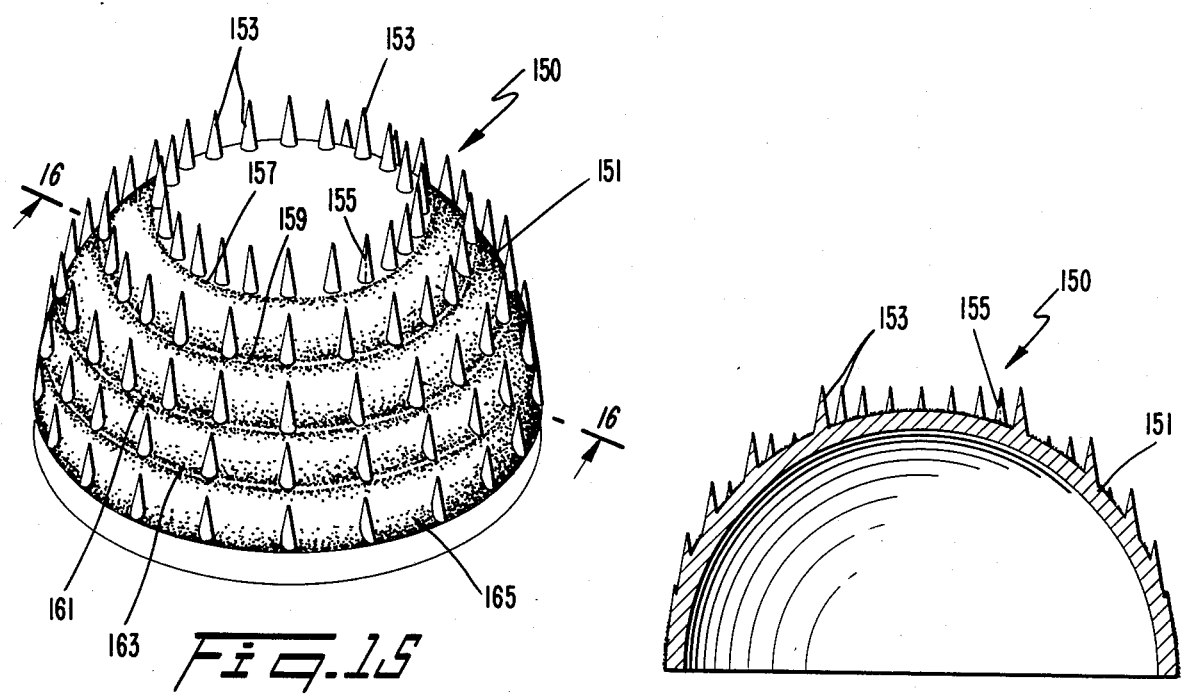

PROSTHESIS INTERFACE SURFACE AND METHOD OF IMPLANTING

BACKGROUND OF THE INVENTION

This invention relates to an improved prosthesis interface surface and the method of implanting it in conjunction with an artificial joint replacement procedure. At present, the majority of total joint components are stabilized with methyl methacrylate bone cement which functions as a mechanical interlock between the associated bone and the replacement joint. Most of these total replacement prostheses have been for hip and knee joints and the designs utilized involve combinations of plates, stems and/or peg structures to achieve fixation. Since the replacement joints have little or no inherent stability without cement, the usual insertion procedures include production of oversized holes and filling the holes with cement during implantation. Several disadvantages of implants which require cement have been documented as follows:

(1) The single most frequent failure mode of cemented implants has involved the loosening and subsequent failure thereof. While the rate of loosening varies with component design and surgical techniques, loosening has universally been reported to be a major limiting factor to long term success of the implant.

(2) The major disadvantages with cemented implant designs are: loosening or fragmentation at the bone-cement or prosthesis-cement interface; difficulty in removing cement in affected patients or in previous replacement failures that need revision; poor mechanical properties of methyl methacrylate cement in that while it resists compression well, it responds poorly to torsion, shear and tension; susceptibility of blood, fluids or air to be trapped in the cement to thereby cause stress risers and thus reduce fatigue strength; difficulty in controlling penetration of the cement—while recent work has shown that pressurizing the cement improves fixation to trabecular bone, the preparation of a clean trabecular bone surface is critical and is difficult to achieve; the enlarged opening required for cement insertion requires the sacrifice of a substantial amount of trabecular bone; and the physiological affects of methyl methacrylate cement which in operation is a thermo setting acrylic are still as yet unknown.

A second class of prosthesis interface is designed to be used with no associated cement. This class includes several hemiarthroplasties of the hip as well as the total knee tibial component which comprises a polyethylene structure with two large pegs. The pegs are driven into undersized holes and include fins thereon which are designed to provide stable fixation of the implant. The main draw back to these interference fit type designs is the fact that they utilize large protrusions, such as, stems or pegs which may concentrate stress in some areas and cause stress relief in others. Bone remodeling responses to these stress patterns may cause disadvantages bone substance reorientation and subsequent failure of both the bone and the implant.

A further and more recent class of implants have been developed which include a porous surface coating made from porous metal, polyethylene or ceramic materials. These implants have been used as hip and knee joint replacements as well as in conjunction with fixture of dentures. Basically, this class of devices has similar design to that of cemented implants except that a porous material is used at the interface. While the porous implants have not been use long enough to provide good statistical evaluations, several disadvantages have become evident recently:

(1) Bony ingrowth into the surface of the prosthesis has been reported to occur only if the implants are extremely stable and secured for three to eight weeks. In situations where movement of the components has occurred, a fibrous interface may form on the bone and thus cause a loose component. If this occurs, post-operative patient mobility may be severely compromised.

(2) The prosthesis as presently designed needs an extremely accurate initial fit and as such require tedious and sometimes difficult surgical techniques to achieve such a fit.

(3) The geometries of present implant designs do not optimize or maximize the potential porous surfaces and thus limit the amount of bony ingrowth to a limited surface area which reduces the strength of the bond between the implant and the associated bone.

A further group of components include designs which utilize screws or staples to augment the fixation thereof. Additionally, artificial ligaments have been designed which contain metallic bony insertions. These components have disadvantages as requiring accuracy in fabricating the screw holes or the receiving surfaces for the staples and further the screws may act to crack the bone tissue.

Applicants are aware of the following prior art:

U.S. Pat. No. 2,910,978 to Urist discloses a hip socket having a plurality of anchoring spikes 19 which project the exterior bottom of the shell 15. The spikes 19 provide a simple interference fit as the sole means for maintaining the socket in position. The device of Urist is different from applicants' invention because, firstly, in applicants' invention, the interference fit is only used on a temporary basis while the bony growth is forming; secondly, the device of the present invention provides a contact stress spectrum or gradient to assure an optimum ingrowth environment. This contact stress gradient is a design feature determinate for the shape, size and array of cones, a concept not confronted by Urist; thirdly, the device of the present invention is not limited to hip implants but rather is applicable for any type of prosthetic body implant.

U.S. Pat. No. 3,683,421 to Martinie discloses a prosthetic joint assembly wherein the bone attachment socket is provided with a plurality of apparently conical projections 62 (FIG. 4) which are designed to more firmly secure the socket to the associated acrylic cement. The patent to Martinie is obviously quite different to the teachings of the present invention since there is no disclosure therein of porous coatings, bone ingrowth, contact stress or sequence of interference in permanent ingrowth fixation.

U.S. Pat. No. 3,728,742 to Averill discloses a knee or elbow prosthesis including a bone contact surface which is provided with serrations 32 to assist in the firm anchorage by the associated cement. As is seen in FIG. 6 of Averill, the serrations are in no way related to the configuration of the surface of the present invention. Further, there is no disclosure in Averill of the concept of ingrowth of bony tissue.

U.S. Pat. No. 3,808,606 to Tronzo discloses a plurality of embodiments of bone implants wherein a porous exterior surface is provided to permit ingrowth of bone for secure fixation. As disclosed therein the porous exterior surface may be made of stainless steel, titanium or titanium alloys which may be applied as a powder and then sintered, if desired. The present invention differs from Tronzo in that (1) Tronzo does not disclose a configuration of conical projections like that of the present invention, (2) Tronzo does not treat a specific design for contact stress on the associated bones, (3) Tronzo does describe the use of an interference fit preliminary to ingrowth fixation but differs in the way that this is accomplished and (4) No provision is made for an optimal interface between the prosthesis and the associated bone.

U.S. Pat. No. 3,869,731 to Waugh, et al. discloses a tibial implant including concentric rings which bite into the tibial bone. There is no disclosure in this patent of ingrowth or a porous coating to facilitate bony ingrowth. The concentric rings as best shown in FIG. 7 bear no resemblance structurally or functionally to the teachings of the present invention.

U.S. Pat. No. 4,021,864 to Waugh discloses an ankle prosthesis including a tibial member provided with truncated pyramidal teeth 20 best shown in FIGS. 6 and 7 which enhance the retention in the bone in conjunction with a suitable bone cement. Obviously there is no concept disclosed in Waugh of the use of a porous prosthetic surface to facilitate the bony ingrowth nor any disclosure of the specific structure disclosed in the present invention.

U.S. Pat. No. 4,166,292 to Bokros discloses a stress reinforced artificial joint prosthesis made preferably of graphite with a pyrolytic carbon coating. As shown, the prosthesis includes ridges 24 of triangular cross-section which are provided to enhance the permanent fixation of the prosthesis. It is believed that the use of the graphite substrate is more related to a concept of shock absorption or trying to match the prosthetic elastic modulus or stiffness to that of the bone. This concept in no way relates to ingrowth fixation, a spectrum of contact stress or any other concepts disclosed herein.

U.S. Pat. No. 4,231,120 to Day discloses an endoprosthetic orthopedic device having a method of securement involving an elongated stem with annular or helical fin-like elements extending radially outwardly therefrom. This device is inserted into a slightly undersized recess in the bone and the fins provide fixation therein. With regard to this patent, it is noted that no use of porous coated metal is described therein. True ingrowth into 100 to 400 micron pores is not used. The prosthetic component of Day is made of polyethylene and the fixation technique described therein involves defomation of this large polyethylene peg.

U.S. Pat. No. 4,309,777 to Patil discloses an artificial intervertebral disc employing spikes 18 and 22 on the upper and lower surfaces thereof for engagement with the respective vertabra. Springs 16 within the device provide the force necessary to insert the spikes in the vertebra. With regard to Patil, the above described projections are not coated with any porous material and rely solely upon interference fit for securement into the respective vertebra.

U.S. Pat. No. 4,355,429 to Mittelmeier, et al. discloses a slide prosthesis for the knee joint which is secured without cement. Anchoring pins are integrally provided and refer to by reference numerals 21 and 22 and have a profile-like out of a bone screw. These pins are inserted into slightly undersized holes drilled into the bone. If desired, the contact surface may be covered with a coating of bio-active particles. In this patent, the prosthesis is made of carbon fiber, reinforced plastics or aluminum oxide ceramic covered with bio-active particles. There is no disclosure of covering of the bone engaging surfaces of the prosthesis with a porous coating material. There is no disclosure therein of a specific design for a spectrum of contact stress nor is a sequence of interference giving away to durable ingrowth fixation described.

SUMMARY OF THE INVENTION

As such, an invention has been disclosed herein which overcomes the drawbacks of the prior art as described above by providing the following combination of features:

(A) The prosthesis interface surface of the present invention is composed of a multiplicity of modified conical projections located in close proximity to one another and with substantially parallel longitudinal axis. The conical projections may have either a convex, concave or a straight profile and the dimensions thereof may be varied according to the particular application. Generally speaking, the axial length of the conical projections should be greater than the diameter of the base portions thereof and this configuration will give the entire prosthesis interface surface a multiple spike-like geometry.

(B) The entire prosthesis interface surface including both the conical projections and the areas between the conical projections is coated with or alternatively is made from a porous material with the pores thereof being specifically selected to optimize bony ingrowth of bone tissue. The combination of the plurality of conical projections and the porous surface not only facilitates the immediate stability of the prosthesis but optimizes porous ingrowth by achieving a substantially greater contact surface area than presently known.

(C) The stability of the prosthesis interface surface results from its design geometry as well as from the specific technique of insertion thereof. In this regard, one aspect of the invention lies in the use of a pilot driver including conical projections corresponding to the conical projections of the implant but slightly smaller in configuration. The pilot driver is impacted into the bone by a suitable tool to thereby produce slightly undersized conical spaces. When the implant is then impacted with the respective conical projections being forcibly inserted into the respective undersized conical recesses. The interference fit thereby created provides immediate stability.

(D) In cases where the areas of sclerotic hard bone are present on the bone interface surface so as to prevent the utilization of the pilot driver, a modified drill guide may be utilized which instead of including undersized conical projections rather includes drill hole guides which correspond to the proposed locations of the conical projections of the implant. When this drill hole guide is used, slightly undersized drill holes may be made therethrough and into the bone interface surface so that the prosthetic implant may be impacted onto the surface and attached thereto with an appropriate interference fit.

The prosthetic interface surface of the present invention provides a number of significant advantages over prior art designs:

(1) The surface provides immediate stability from implantation which promotes bony ingrowth.

(2) The prosthetic interface surface provides a large contact surface through the use of conical projections to optimize bony ingrowth and distribute stress evenly across the entire interfacial region.

(3) The prosthetic interface surface does not use cement and consequently avoids all of the disadvantages of using methyl methacrylate cements with their high temperature curing characteristics and thereby may avoid undue bone stresses during the curing and thus provide a longer lasting implant.

(4) The surface configuration disclosed herein provides a spectrum, scale, array or gradient of contact stress to the patient's trabecular bone to optimize ingrowth effectiveness and promote stress-induced strengthening of the supporting trabecular bone. As described, the point of each of the cones provides a very small surface area so that with even moderate forces imposed thereon, the contact stress (or force per unit area) is very great at that region. The base of the cones and the area between the cones has a large surface area such that with similar imposed forces to the moderate forces described above, the contact stress in this region would be quite small by comparison. Bone cannot tolerate excessively large contact stresses and it also tends to recede or atrophy in the face of excessively small contact stresses imposed thereon. The provision of a scale or gradient of contact stress assures that a considerable proportion of the working surface of the prosthetic implant will be at the optimal stress level. In this situation, the bone tissue picks out the region on the conical protrusions thereof which has the most desirable stress level and ingrows there and strengthens there with time, while ingrowing at other regions of the implant to a somewhat lesser extent. The concept disclosed in this section is incorporated in all prosthetic implant components incorporating the present invention therewith.

(5) The method of implantation of a prosthesis including the surface of the present invention is simplified which would reduce the probability of technical errors and may also reduce operating time.

(6) Since the prosthetic interface surface is designed primarily for non-cemented implants, surface preparation is simplified.

(7) In conjunction with (6) above, the lack of cement reduces the sacrifice of trabecular bone which would ordinarily be necessary to provide a recess for the cement.

Several modifications may be made to the teachings of the present invention without departing from the intended scope thereof. For example, the size of the conical projections as well as their profile, whether straight, concave or otherwise, may be altered to optimize insertion thereof or stability. Further, the prosthetic interface surface may be made porous by any technique available to manufacturers, such as, for example, sintering, fiber incorporation, ceramic coating, micro pore dusting and any other manufacturing technique. If desired, the prosthetic interface surface could also be used where appropriate in total or partially cemented applications. It is to be noted in this regard that this is a peripheral purpose of the present invention which is mainly to be used without cement as described herein. Further, if desired, the prosthetic interface surface may also be used for the implantation of tendons, ligaments or dentures.

Accordingly, it is a first object of the present invention to provide an improved prosthesis interface surface usable with any implantable components where stable, long lasting fixation to bone is needed.

It is a further object of the present invention to provide an improved prosthetic interface surface which includes a plurality of substantially conical protrusions designed to increase the surface area of the prosthetic interface with the bone.

It is a further object of the present invention to provide an improved prosthetic interface surface which includes a porous surface to facilitate bony ingrowth and thereby facilitate retention of the prosthetic implant.

It is a yet further object of the present invention to provide the porous surface by coating a base therewith.

It is a yet further object of the present invention to provide an improved prosthetic interface surface which enables the combination of both an interference fit and bony tissue ingrowth thereto.

It is a yet further object of the present invention to provide an interface surface usable with prosthetic implants which provides a spectrum, scale, array or gradient of contact stress to the trabecular bone in which it is installed, thereby allowing the bone tissue to choose the region on the interface surface having the optimum stress level, at which region the bone tissue will ingrow thereon and strengthen over time.

It is a still further object of the present invention to provide a new improved method of implanting a prosthesis including the surface of the present invention.

It is a yet further object of the present invention to provide such a method which includes the use of a special pilot driver including conical projections slightly smaller than the prosthesis projections to enable the above described interference fit.

It is a yet further object of the present invention to provide a further method of implantation including the use of a drill hole guide in situations where areas of sclerotic hard bone are present on the bone interface surface.

These and other objects, advantages and features of the present invention may be better understood by reading the following detailed description of the preferred embodiments in conjunction with the appended drawing figures.

BRIEF DESCRIPTION OF THE DRAWINGS

FIG. 5 shows a cross-sectional view along the line 5—5 of FIG. 3.

FIG. 6 shows an enlarged perspective view of one of the fins shown in the femoral component of FIGS. 3-5.

FIG. 7 shows a front view of the tibial component shown in FIG. 1.

FIG. 8 shows a bottom view of the tibial component shown in FIG. 1.

FIG. 9 shows a single substantially conical pin used in one embodiment of the present invention.

FIG. 10 shows a side view of a pilot driver designed to make pilot holes prior to insertion of the tibial component shown in FIGS. 1, 7 and 8.

FIG. 11 shows a bottom view of the tibial pilot driver of FIG. 10.

FIG. 12 shows a pin utilized in conjunction with the tibial pilot driver of FIGS. 10 and 11.

FIG. 13 shows a top view of a drill guide designed for use with the tibial component described in FIGS. 1, 7 and 8 in situations where the bone is sufficiently hard to preclude use of the tibial pilot driver of FIGS. 10-12.

FIG. 14 shows a cross-sectional view through the line 14—14 of FIG. 13.

FIG. 15 shows a perspective view of the present invention when used in conjunction with an acetabular component.

FIG. 16 shows a cross-sectional view through the line 16—16 of FIG. 15.

SPECIFIC DESCRIPTION OF THE PREFERRED EMBODIMENTS

Figure 1:
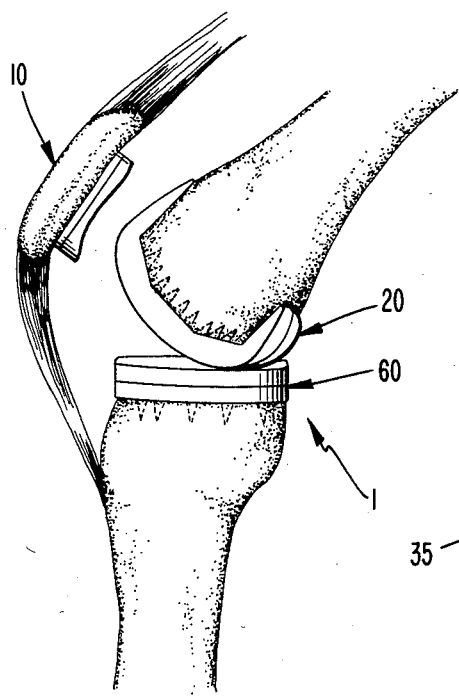
FIG. 1 shows a perspective view of a total knee prosthesis including femoral component, tibial component and patella component, each of which incorporates the present invention therein.
Figure 2:
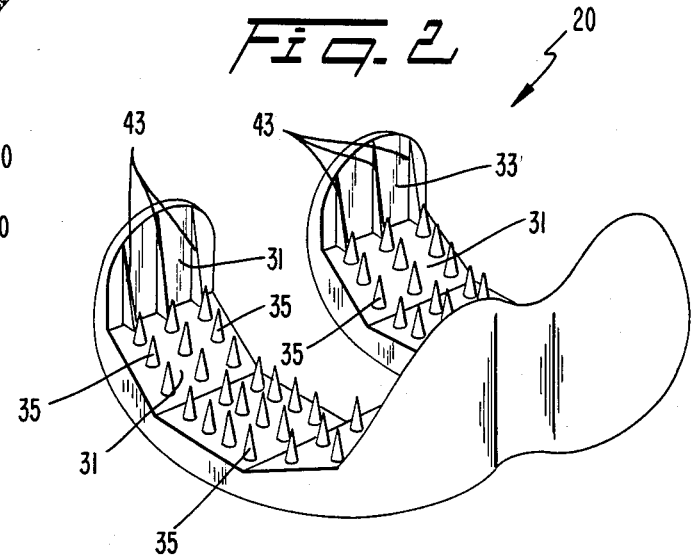
FIG. 2 shows a perspective view in the direction of the posterior condylar surface of a femoral component in accordance with the present invention.
Figure 3:
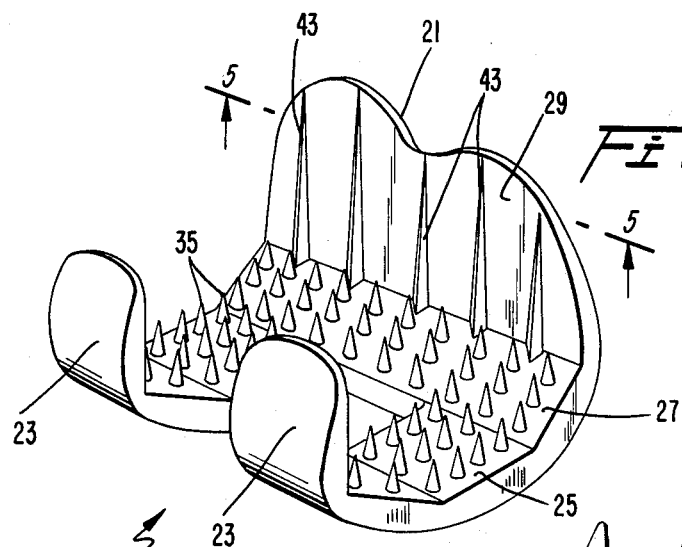
FIG. 3 shows a perspective view in the direction of the patella-femoral flange of the femoral component also shown in FIG. 2.
Figure 4:
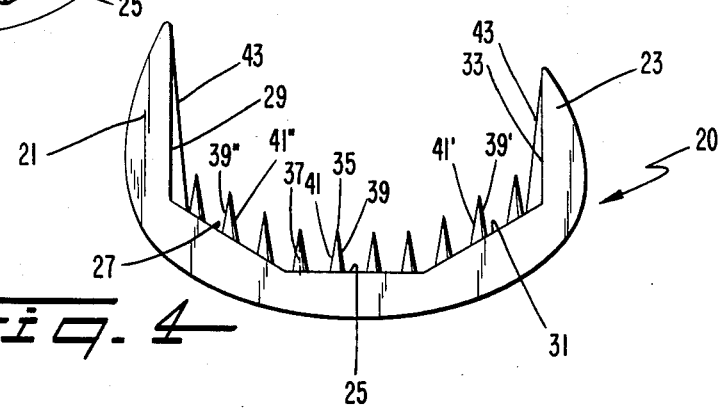
FIG. 4 shows a side view of the femoral component of FIGS. 3 and 4.

FIG. 1 shows a total knee prosthetic replacement including a patellar component 10, a femoral component 20 and a tibial component 60. With reference to FIGS. 2-6, the details of the femoral component will be set forth, with it being clearly understood that the details of the present invention as applied to the femoral component are applicable to any body implant. The femoral component 20 is seen to include a patella-femoral flange 21 and vertical condylar extensions 23. In the interior of the component, an interface surface is provided formed at least partially of a flat surface 25 which is connected to a substantially flat interior surface 29 of the patella-femoral flange 21 by an angular inner surface 27. On the other side of surface 25, the interface surface continues with each of the vertical condylar extensions having an angled surface 31 and a further surface 33 substantially parallel to the above mentioned surface 29 on the patella-femoral flange 21. Surfaces 27 and 31 each form obtuse angles where they meet surface 25. As is seen especially in FIGS. 2, 3 and 4, the surfaces 25, 27 and 31 can be seen as respective subregions of a first type of interface surface because they are each provided with a plurality of conical projections 35 extending therefrom. As best seen in FIG. 4, the conical projections 35 on the surface 25 extend directly upwardly and each conical projection 35 includes a central axis 37 which is substantially parallel to the axes 37 of all other conical projections 35. Also, as best shown in FIG. 4, the projections 35 on the respective surfaces 27 and 31 also include axes 37 which are substantially parallel to the axes 37 on all previously mentioned conical projections 35. In order to maintain the axes 37 on the conical projections 35 which are mounted on the surfaces 27 and 31 parallel with the axes 37 on the conical projections on the surface 25, the projections 35 on the inclined surfaces 27 and 31 appear to be at least partially embedded into the respective surfaces 27 and 31. As such, while the conical projections 35 on the surface 25 include side wall portions 39 and 41 of substantially equal length, the conical projection 35 on the angled surface 27 include surfaces 39' and 41' which differ in length, and similarly, the conical projections 35 on the angled surface 31 include surfaces 39" and 41" of differing lengths. This configuration enables the axes 37 of all of the conical projections 35 to be substantially parallel to one another.

It has been determined that the surfaces 29 and 33 of the respective patella-femoral flange and vertical condylar extensions should also include surface projections to enhance the retention of the femoral component on the end of the femur. However, due to the fact that the surfaces 29 and 33 are substantially parallel to the direction in which the component is impacted into its installed position, substantially conical projections may not be used on the surfaces 29 and 33. As such, instead, fins 43 are employed for these surfaces. FIG. 6 shows a single fin 43 protruding from a surface, for example, the surface 33, a small portion of which is shown in FIG. 6. The fin 43 includes a substantially triangular base portion 45 defined by two sides 47 of the fin and the face of the surface 33. The uppermost portion of the fin 43 is defined by a substantially pointed area 49 which connects with the faces 47 of the base 45 by way of substantially triangular faces 51. The triangular faces 51 merge together at an innersecting linear portion 53 which connects the points 48 and 49 together. Since the point 48 is on surface 27, or one of surfaces 31, but is spaced from surface 33, and the point 49 is on the surface 33, the linear portion 53 is wedge-like and provides a wedging action with the bone surface when the femoral component 20 is installed thereon. This second type of projection therefore communicates with surface 33 of the interface surface throughout its length. As will be further explained hereinafter, the femoral component 20 is installed onto the end of the femur bone by forcing it thereon with a linear motion. Prior to the installation of the femoral component 20 onto the femur, the end of the femur is prepared for such installation through the forming of pilot holes designed to provide an interference fit with the conical projections 35 and pilot recesses designed to provide an interference fit with the fins 43. The process of forming such holes and recesses will be further described in conjunction with the specific description of the tibial component 50 below. FIG. 5 shows a cross-sectional view through the patella-femoral flange 21 and shows a cross-section through the fins 43. As shown in FIG. 5, the surfaces 51 and the linear portion 53 form, with the surface 33, a substantially triangular configuration which, as will be better understood in conjunction with FIG. 6, decreases in size as one moves upwardly toward the point 49.

Referring now to FIGS. 1 and 7-14, the details of the tibial component 60 and its method of installation will be described. With reference to FIGS. 7 and 8, the tibial component 60 is seen to include a top surface 61 designed for bearing engagement with the outer surface of the femoral component 20, and further includes a bottom surface 63. As best seen in FIG. 8, the tibial component 50 is approximately U-shaped with legs 65 connected together by connecting portion 67. The bottom surface 63 includes a large number of substantially conical projections 69 each of which having an axis 71 with the axes 71 being substantially parallel to one another. The parallel nature of the axes 71 enables the tibial component to be installed on a bone surface of the tibia by linearly forcing the substantially conical projections 69 into pre-formed substantially conical holes in the bone surface which are made slightly smaller than the substantially conical projections 69 to ensure an interference fit therein. At this point, it is noted that the conical projections 69 of the tibial component 60, the substantially conical projections 35 and fins 43 of the femoral component 20, and all other such substantially conical projections and/or fins as contemplated by the present invention each have on the surface thereof a porous material specifically designed to enhance bony ingrowth therein to assist in maintaining the respective prosthetic components in their originally mounted positions. In this regard, the surfaces thereof may be made porous by any technique desired, such as, for example, sintering, fiber incorporation, ceramic coating, micro pore dusting and any other desired means. Further, it is noted, that the substantially conical projections and/or fins may be entirely made of a material which is porous in nature, if desired.

If desired, the tibial component 60 shown in FIGS. 7 and 8 may be made of a single forged or molded piece including the projections 69 as an integral part of the molding. Alternatively, in situations where conical projections 69 of differing configurations for differing situations may be required, the substantially conical projections 69 may be formed as separate entities insertable into holes (not shown) in the bottom 63 of tibial components 60. In this vein, attention is directed to FIG. 9 which illustrates a typical substantially conical projection 69. As seen in FIG. 9, the projection 69 includes the above described axis 71 and is formed as an integral part of a base portion 73. The base portion 73 includes a substantially cylindrical wall 75 and a flat wall 79 connected thereto through a substantially conical wall 77. The substantially conical projection 69 protrudes from a substantially flat surface 81 and is seen to include an annular radiused portion 83 emerging from the surface 81 which itself merges into a conical surface 85 which merges into a radiused, substantially semi-spherical tip portion 87. The holes formed in the surface 63 of the component 60 are made slightly smaller in diameter than the base portion 73 of the member 69 so that the member 69 may be inserted into these openings (not shown) in a press-type fit. As shown in FIG. 9, the surface formed by the portions 83, 85 and 87 of the substantially conical projection 69 is porous in nature so as to enhance the ingrowth of bony tissue as explained above.

With reference now to FIGS. 10, 11 and 12, a pilot driver 100 is shown which may be used to create the pilot holes within the bone tissue which are necessary to enable insertion of the substantially conical projections of the tibial component 60. The pilot driver 100 includes a bottom surface 101, a top surface 103 and a post-like member 105 extending outwardly from the top surface 103. The post-like member 105 is provided so that the pilot driver 100 may be attached to a suitable device which will enable the pilot driver 100 to be impacted against the desired bone tissue so as to create the pilot holes for the substantially conical projections of the tibial component 60. As best shown in FIG. 10, the bottom surface 101 includes a plurality of pins 107 of slightly smaller dimension than the substantially conical projections 69 of the tibial component 60 so that the substantially conical projections 69 will form an interference fit with the holes formed by the projections 107. As best seen in FIG. 11, the bottom surface 101 has approximately the same configuration as the bottom surface 63 of the tibial component 60. This bottom surface 101 includes leg portions 109 connected together by connecting portion 111. Member 105 may be made of any cross-section enabling it to be connected to an appropriate impacting tool, such as, for example, round, square, hexagonal, etc. The projections 107 may be formed integrally with the pilot driver 100, or alternatively, the projections 107 may be formed as separate pins insertable into holes (not shown) in the surface 101 of the pilot driver 100. In this regard, references made to FIG. 12 which shows a typical pilot drive pin 107. The pin 107 includes a base portion 113 including a substantially cylindrical outer surface 115 which surface 115 is connected to a flat bottom surface 119 through a substantially conical surface 117. The base portion 113 includes a top surface 121 which merges with the projection at an annular radiused portion 123. The above described structure is substantially identical to the corresponding structure of the base portion 73 of the substantially conical projection 69 described above. The annular radiused portion 123 merges into a substantially conical portion 125 of the projection 107 and is made of substantially the same angular configuration as the substantially conical projection 69 discussed above. The portion 125 terminates at a sharp point 127 as contrasted with the rounded end 87 of the substantially conical projection 69. This pointed end 127 enables the projection 107 to form an opening of similar configuration in the bone tissue when impacted therein by a suitable device (not shown) the angle of the surface 125 being similar to the angle of the surface 85 of substantially conical projection 69 enables the substantially conical projection 69 to fit into the hole formed by the projection 107 with an interference type fit the interference of which is increased as the projections 69 are pushed further and further into the holes formed by the projection 107. It is noted that the concepts taught by the pilot driver 100 which is specifically designed to form pilot holes for receipt of the projections on a tibial component 60 may also be applicable to any pilot driver designed for any implantable prosthetic component, such as, for example, an acetabular component, a patellar component or a femoral component. The main thing that all pilot drivers must have in common is the placement of projections so as to enable forming holes in bone tissue through linear movement thereof only.

Under certain circumstances, the bone tissue in the region where the component is to be implanted is too hard to enable the successful use of the pilot driver. In the case of the tibial component, this problem would be remedied through the use of a tibial drill guide illustrated in FIGS. 13 and 14. The tibial drill guide 130 shown in FIGS. 13 and 14 is basically a template with holes in it which allow accurate location of pilot holes for tibial component projections 69. The drill guide 130 includes a top surface 131, a bottom surface 133, and a peripheral edge 135. As best shown in FIG. 13, the top surface 131 as well as the bottom surface 133 are made of approximately the same configuration as the surface 63 of the tibial component 60 and includes leg portions 137 connected by a connecting portion 139. The drill guide 130 includes a plurality of holes 141 extending therethrough and of a diameter enabling extension therethrough of a drill bit of appropriate size to drill substantially conical holes within the hard bone tissue which will enable the projections 69 of the tibial component 60 to fit therein with an interference fit. In use, the tibial drill guide 130 is placed over the region where the holes are to be drilled and is fastened there by any suitable means. After the drill guide 130 is fastened into position, the holes are drilled after which the tibial component 60 is impacted linearly into its fixed position. It is noted, that the concepts taught by the tibial drill guide 130 are equally applicable to a drill guide formed to make holes for receipt of substantially conical projections in any implantable prosthetic component.

FIGS. 15 and 16 illustrate a further embodiment of the present invention which is intended to be used in conjunction with an acetabular component, more commonly known as a hip socket replacement joint. Referring to FIGS. 15 and 16, the acetabular component 150 is seen to comprise a substantially semi-spherical surface 151 which comprises a porous surface to enhance ingrowth of bone tissue therein. In the preferred embodiment, the porous surface comprises a porous layer of an alloy including a combination of titanium, aluminum and vanadium marketed under the registered trademark TIVANIUM by Zimmer, Incorporated. As shown, the surface 151 has extending outwardly therefrom, a series of rings of conical projections 153 each of which has an axes 155 therethrough. The conical projections in this embodiment of the invention are generally similar to those shown in the embodiment of FIGS. 1-5 in that some such projections are entirely exposed, others appear partially embedded, and others communicate with the surface 151 throughout their longitudinal length. As best seen in FIG. 16, the axes 155 of the respective substantially conical projections 153 are substantially parallel to one another so that the acetabular component 150 may be inserted into the associated bone tissue by a linear motion thereof to thereby cause an interference fit between the respective substantially conical projections 153 and holes formed in the bony tissue for receipt of this substantially conical projections 153.

As best seen in FIGS. 15 and 16, in order that the axes 155 may be parallel, the rings of substantially conical projections take on differing configurations with increasing circumference. As shown in FIG. 15, in the ring 157 the projections 153 are substantially fully exposed while in the ring 165, the projections 153 are as the fins described hereinabove in that they taper longitudnally and are at least partially laterally embedded substantially throughout their lengths within the surface 151. If desired, the projections of the larger rings 163, 165 may be replaced with fins having triangular configurations similar to those fins 43 disclosed inconjunction with the femoral component 20 shown in FIGS. 2-6.

As above, the acetabular component may be installed by forming holes in the bone tissue with either (1) an acetabular pilot driver (not shown), or (2) an acetabular drill guide and a drill with appropriately sized drill bit (not shown) drill, and subsequently linearly forcing the projections 153 into the holes with an interference fit.

The prosthetic interface surface has been disclosed herein in terms of a plurality of conical protrusions each shown in the drawings to include a substantially circular base portion and converging to a radiused tip portion. It is noted here, that this construction of the protrusions is merely one example of the possible configurations of the protrusions which may be utilized within the purview of the present invention. To be within the purview of the present invention, the protrusions must include (1) a base portion of any shape, (2) a body portion convergingly tapering away from the base portion, and (3) a tip portion having a smaller area than the area of the base portion. Further, the longitudinal axes of all of the protrusions must be substantially parallel to one another. As such, the base portion may be elliptical, polygonal (with 3-12 or more sides) or any irregular shape, the body portion may include a flat, concave or convex surface or any combination thereof and the tip portion may be flat to provide a truncated protrusion or as well could be substantially pointed, or of any other configuration, such as, concave or convex. Thus, the protrusions may each comprise a right circular cone, truncated or otherwise, a pyramid with any desired number of sides, truncated or otherwise, an elliptical cone, truncated or otherwise, or any other configuration having the above described three criteria, truncated or otherwise. Alternatively, respective protrusions may each have a unique one of the above described configurations with several configurations being represented on a given prosthesis. Where necessary, the pilot driver and/or drill guide disclosed herein may be appropriately modified to allow the formation of the appropriate holes in the bone tissue for receipt of the various above described potential shapes and configurations for the protrusions.

It is stressed here, that the above described embodiments of prosthetic implants utilizing the interface surface of the present invention are to be considered merely examples of the uses to which the inventive surface may be put. The interface surface may be used with any implantable prosthesis where the goal is a permanent fixation through bony ingrowth therein. The prosthesis incorporating the inventive surface thereon require no cement for fixation and may easily be installed with less surgical time than is normally required for cemented and other implants. As such, various modifications, changes or alterations of the invention disclosed herein may become evident to those skilled in the art and the invention disclosed herein is not intended to be limited by the description hereinabove but rather, is intended only to be limited by the appended claims.

We claim:

1. A prosthetic member for engaging couplingly with bone tissue of a living being, the prosthetic member comprising:
    an interface surface for communicating with the bone tissue, said interface surface having first and second surface regions oriented at a predetermined angle with respect to each other;
    a plurality of first projection members each having a respective portion arranged to project axially along a respective first longitudinal axis and coupled at a base portion thereof to said first surface region of said interface surface, whereby said projection portion extends outwardly from said first surface region of said interface surface; and
    a plurality of second projection members each tapering substantially to a point substantially along said second surface region and having an elongated configuration having a predetermined elongation distance determinable along a respective second longitudinal axis, and being formed integrally with said second surface region of said interface surface whereby each such second projection member is partially embedded along a lateral region thereof which is substantially parallel with said second longitudinal axis in said second surface region, said first and second longitudinal axes of said first and second projection members being substantially parallel with one another.

2. The prosthetic member of claim 1 wherein said first surface region of said interface surface comprises a substantially planar surface subregion.

3. The prosthetic member of claim 2 wherein said first surface region of said interface surface further comprises a further surface subregion arranged to form an obtuse angle with said substantially planar surface subregion.

4. The prosthetic member of claim 3 wherein said further surface subregion is provided with respectively associated ones of said first projection members, such respectively associated first projection members appearing to be partially embedded in said further surface subregion.

5. The prosthetic member of claim 4 wherein said first projection members are formed integrally with said further surface subregion.

6. The prosthetic member of claim 1 wherein said first surface region of said interface surface comprises a continuous first curved surface.

7. The prosthetic member of claim 6 wherein said second surface region of said interface surface comprises a continuous second curved surface.

8. The prosthetic member of claim 7 wherein said continuous first and second curved surfaces join smoothly and continuously with one another.

9. The prosthetic member of claim 1 wherein each of said first projection members have a substantially conical configuration.

10. The prosthetic member of claim 1 wherein at least one of said second projection members communicates at an end thereof with said first surface region of said interface surface.

11. The prosthetic member of claim 10 wherein at least a portion of said interface surface has a porous surface structure.

12. The prosthetic member of claim 11 wherein said porous surface structure is formed by alloy of titanium and vanadium.

* * * * *